(12) United States Patent
Olshansky (10) Patent No.: US 8,720,713 B2
(45) Date of Patent: May 13, 2014

(54) STORAGE CASE FOR ARTICLES

(76) Inventor: Ariane Olshansky, San Anselmo, CA (US)

( * ) Notice: Subject to any disclaimer, the term of this patent is extended or adjusted under 35 U.S.C. 154(b) by 0 days.

(21) Appl. No.: 13/305,694

(22) Filed: Nov. 28, 2011

(65) Prior Publication Data

US 2013/0134063 A1    May 30, 2013

(51) Int. Cl.
*A61J 9/08*    (2006.01)
(52) U.S. Cl.
USPC ....... 215/11.6; 220/4.21; 220/4.22; 220/4.23; 220/4.24; 215/11.1
(58) Field of Classification Search
USPC ............... 220/4.21–4.24, 389, 386, 810; 215/11.1, 11.6; 223/64, 84, 6, 845
See application file for complete search history.

(56) References Cited

U.S. PATENT DOCUMENTS

| | | |
|---|---|---|
| 2,951,621 A | 9/1960 | Cheney |
| 4,270,538 A * | 6/1981 | Murphy ........................ 604/346 |
| 5,556,013 A | 9/1996 | Mayer |
| 5,829,083 A | 11/1998 | Sutton |
| 6,234,368 B1 | 5/2001 | DesForges et al. |
| 6,450,333 B1 * | 9/2002 | McClenahan et al. ... 206/315.11 |
| 6,742,683 B1 | 6/2004 | Phan |
| 7,163,605 B2 | 1/2007 | Chen |
| 7,252,573 B2 | 8/2007 | Mann |
| 7,350,679 B2 | 4/2008 | Radtke et al. |
| 7,597,206 B2 * | 10/2009 | Atkins et al. ................. 220/4.23 |
| 2005/0161455 A1 * | 7/2005 | Studee ........................... 220/266 |
| 2009/0308405 A1 * | 12/2009 | Yamashita .................... 128/890 |
| 2010/0219213 A1 | 9/2010 | Phan |
| 2010/0243686 A1 | 9/2010 | Zhang |

\* cited by examiner

*Primary Examiner* — Anthony Stashick
*Assistant Examiner* — Raven Collins
(74) *Attorney, Agent, or Firm* — Steven R. Vosen (57) ABSTRACT

A case is described for use, for example and without limitation, with a nipple shield or nipple protector. The case, which has an interior volume to contain a nipple shield/protector, generally provides a rigid container to protect a nipple shield/protector and to protect it from the environment. Certain embodiments provide rigid container that may be opened to place or remove a nipple shield/protector and closed to hold the shield/protector with a minimal amount of contact. The case may also include ventilation holes to permit drying of the contents of the case.

16 Claims, 7 Drawing Sheets

STORAGE CASE FOR ARTICLES

BACKGROUND OF THE INVENTION

1. Field of the Invention

The present invention generally relates to storage cases, and more specifically to cases that can store and/or protect articles while providing ventilation and minimizing contact with the case.

2. Discussion of the Background

Some nursing mothers use nipple shields or nipple protectors as an aid for themselves or their babies in nursing. Nipple shields and nipple protectors are generally similar devices that have the shape of and are placed over the mother's nipple and include holes to allow milk to flow.

Nipple shields are generally used as an aid for proper nursing, while nipple protectors are used to protect the nipple from discomfort. These devices are typically smaller than a breast and fit over the nipple and surrounding area. A nipple portion of the shield may partially or fully enclose the mother's nipple. The baby then latches onto the nipple shield and feeds as normal, with the nipple shield at least inhibiting some of the discomfort that may otherwise be experienced upon direct contact of the baby with the mother's nipple.

Thus, for example, some mothers experience discomfort during breastfeeding, particularly due to sensitive, sore and/or irritated nipples. Such discomfort can effect and sometimes hinder suitable nursing of a baby, as well as detract from the maternal experience in providing care to her baby. Other nursing problems from or during nursing include difficulties of nursing from flat or inverted nipples and problems with the baby latching properly. Nipple shields and/or nipple protectors may be used to address these problems.

In general, nipple shields are formed from thin sheets of silicone that is washed and kept clean between uses. Since nipple shields are typically formed from a clear material, they can be easily misplaced. Further, the materials that they are formed of may take some time to dry. The care of nipple shields is problematic for at least these reasons.

Figure 1A:
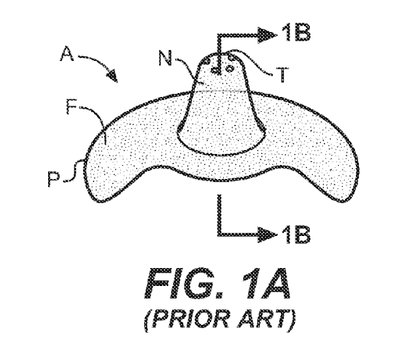
FIG. 1A is a top perspective view of a prior art nipple shield.
Figure 1B:
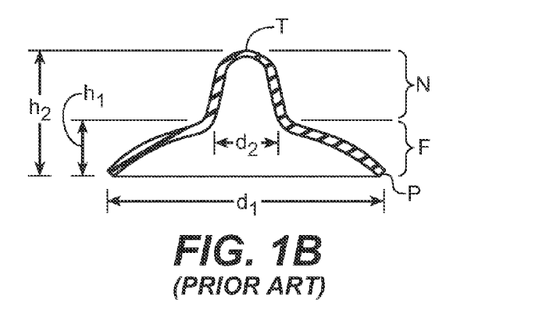
FIG. 1B is a sectional view 1A-1A of a prior art nipple shield.

An example of a prior art nipple shield is illustrated in the top perspective view of FIG. 1A and the sectional view 1A-1A of FIG. 1B. Examples of nipple shields include nipple shields and contact nipple shields manufactured by Medela, Inc. (McHenry, Ill.). As illustrated in FIG. 1B, nipple shield A has an outer, slightly domed portion F with a perimeter P, and a peaked central portion N with at tip T. Perimeter P is generally confined within a circular diameter d1 and extends a height h1 above the perimeter. Peaked portion N is confined within a smaller diameter d2 and extends to a height h2 above perimeter P. In general, the dimensions of nipple shields and nipple protectors are approximately as follows: d1 is 75 mm; d2 is 20 mm, h1 is 20 mm, and h2 is 45 mm.

Prior art cases are not designed to minimize contact between nipple shields and the case and do not allow for ventilation and/or drying of the nipple shield. There exists a need for cases that can protect articles while minimizing contact with the case and allowing for ventilation and/or drying in a protected environment.

In addition, other articles, such as nipple protectors and dental retainers, could also benefit from a case that provides protection from the environment while allowing for ventilation, and which minimizes contact with the case.

BRIEF SUMMARY OF THE INVENTION

The present invention overcomes the disadvantages of prior art by providing a case that can securely hold articles while allowing for ventilation and/or drying of the articles. The case includes an integral drying rack and holes for ventilation and/or dying. Certain embodiments may be easily opened with one hand.

Certain embodiments provide a case for storing articles such as nipple shields or nipple protectors. Certain other embodiments provide a case that conforms to the shape of the article. Yet certain other embodiments provide a case that is rigid, to provide protection, and has holes therethrough to provide ventilation for the interior of the case.

Certain embodiments provide a case having an interior surface for confining an article. The case includes a first case portion and a second case portion adapted for engaging the first case portion to define the interior surface. The first case portion includes one or more first ridges having edges that protrude towards the second case portion and one or more apertures to the exterior of the case. The second case portion includes one or more second ridges having edges that protrude towards the first case portion. The case is configured such that an article placed within the case contacts the edges of at least some of the first ridges and the edges of at least some of the second ridges.

Certain other embodiments provide a case for confining a conical-shaped article. The case includes a first case portion, a second case portion, and a hinge connecting the first case portion and the second case portion, such that when the first case and the second case are in a closed configuration the case has an interior surface. The first case portion has a first rim and includes one or more first ridges having edges that protrude towards the second case portion, where the edges of the one or more first ridges generally define a convex shape, and one or more apertures to the exterior of the case. The second case portion has a second rim and includes one or more second ridges having edges that protrude towards the first case portion, where the edges of the one or more second ridges generally define a concave shape. The case is configured such that article placed within the case contacts the edges of at least some of the first ridges and the edges of at least some of the second ridges.

These features together with the various ancillary provisions and features which will become apparent to those skilled in the art from the following detailed description, are attained by the case of the present invention, preferred embodiments thereof being shown with reference to the accompanying drawings, by way of example only, wherein:

Reference symbols are used in the Figures to indicate certain components, aspects or features shown therein, with reference symbols common to more than one Figure indicating like components, aspects or features shown therein.

DETAILED DESCRIPTION OF THE INVENTION

Although certain preferred embodiments and examples are disclosed below, it will be understood by those skilled in the art that the invention extends beyond the specifically disclosed embodiments to other alternative embodiments and/or uses of the invention and obvious modifications and equivalents thereof. Thus it is intended that the scope of the invention herein disclosed should not be limited by the particular disclosed embodiment described below.

Figure 2:
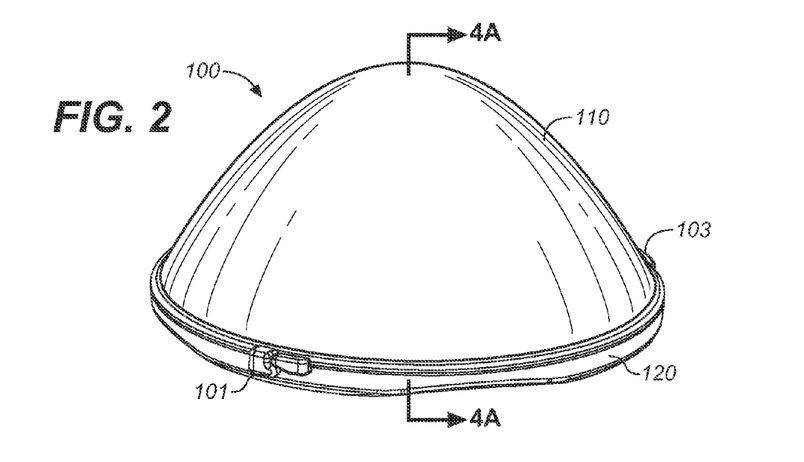
FIG. 2 is a top perspective view of a first embodiment of a case in a closed configuration.
Figure 3:
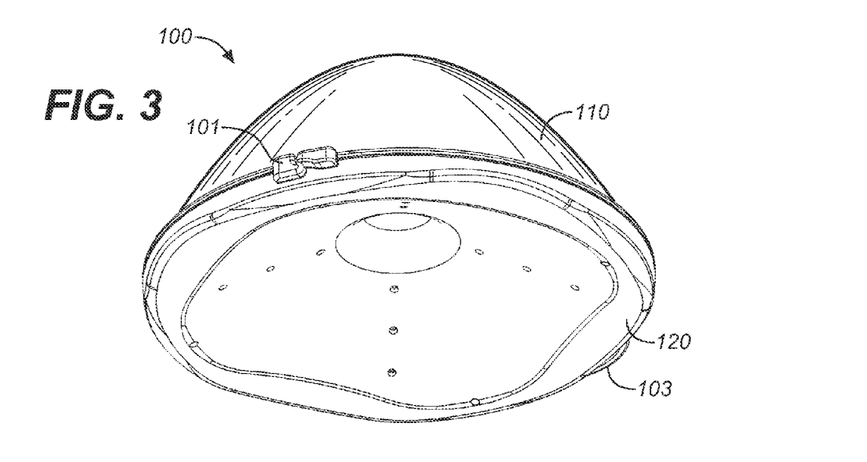
FIG. 3 is a bottom perspective view of the case of FIG. 2.
Figure 4A:
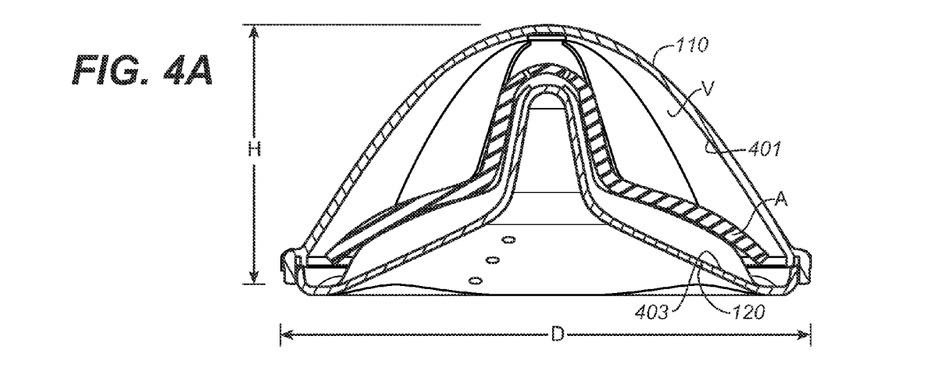
FIG. 4A is a sectional view 4A-4A of FIG. 2.

As an example of a first embodiment of the inventive case 100, FIG. 2 is a top perspective view of the case in a closed configuration, FIG. 3 is a bottom perspective view of the case of FIG. 2; and FIG. 4A is a sectional view 4A-4A of FIG. 2.

Case 100 includes a first case portion 110, which is the top of the case, and a second case portion 120, which is the bottom of the case. Case portions 110 and 120 are joined at a hinge 103 and include a clasp 101 to keep case 100 closed. In FIGS. 2, 3, and 4A, case 100 is in closed configuration defining an internal volume V, defined by bounding top surface 401 and bottom surface 403, and which is large enough to contain an article which is shown, for example and without limitation, as a prior art nipple shield A. In one embodiment, case 100 has dimensions of D=8 mm and H=50 mm.

Figure 4B:
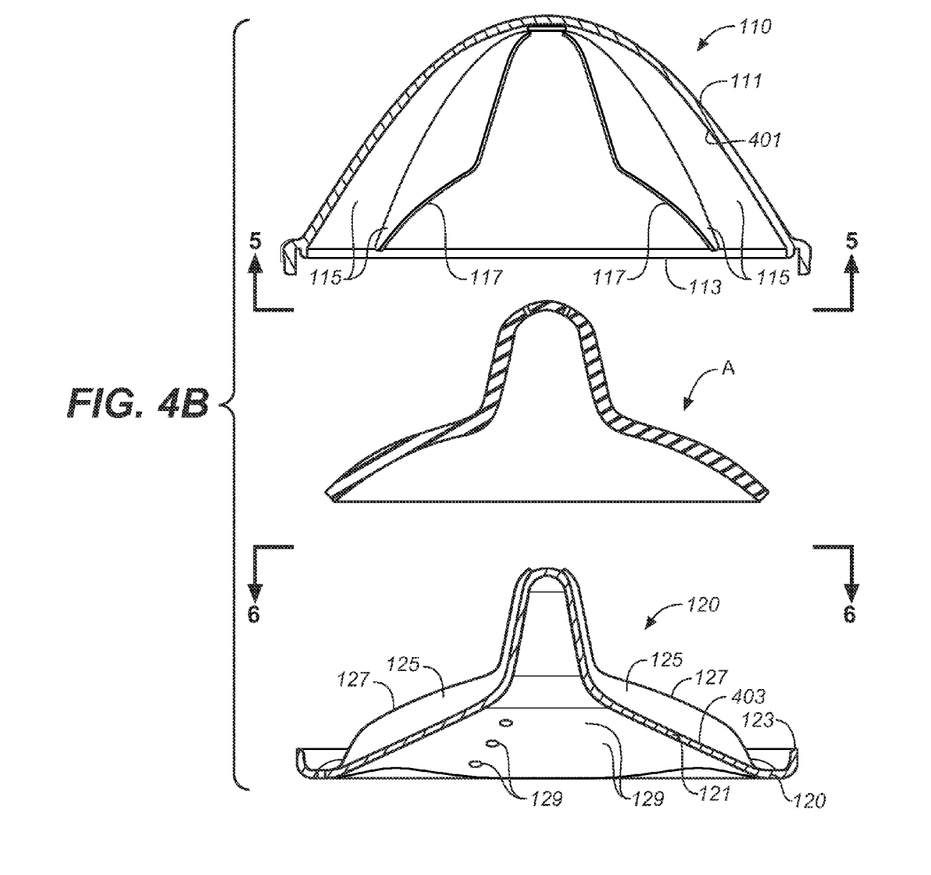
FIG. 4B is an exploded sectional view of FIG. 4A.
Figure 5:
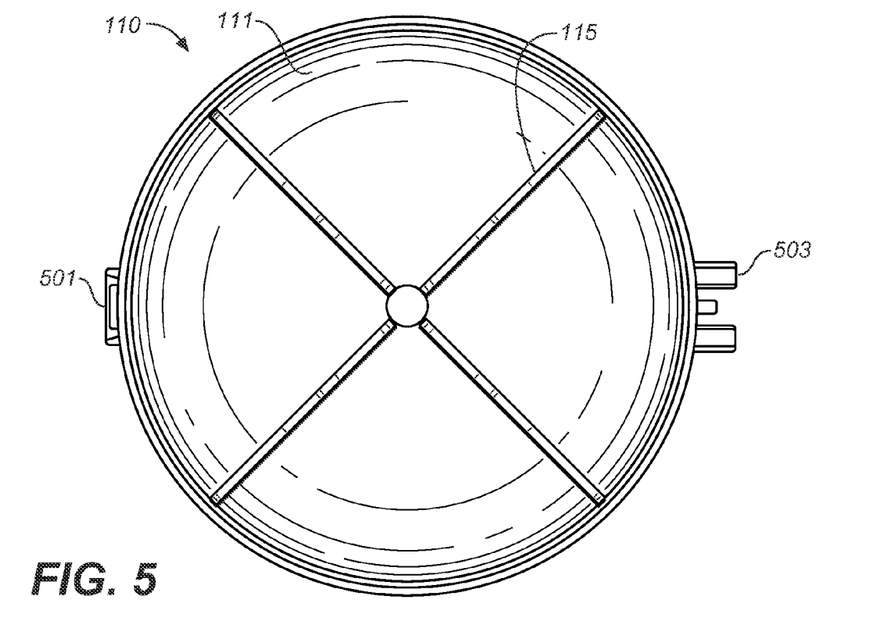
FIG. 5 is a bottom view 5-5 of the case top of FIG. 4B.
Figure 6:
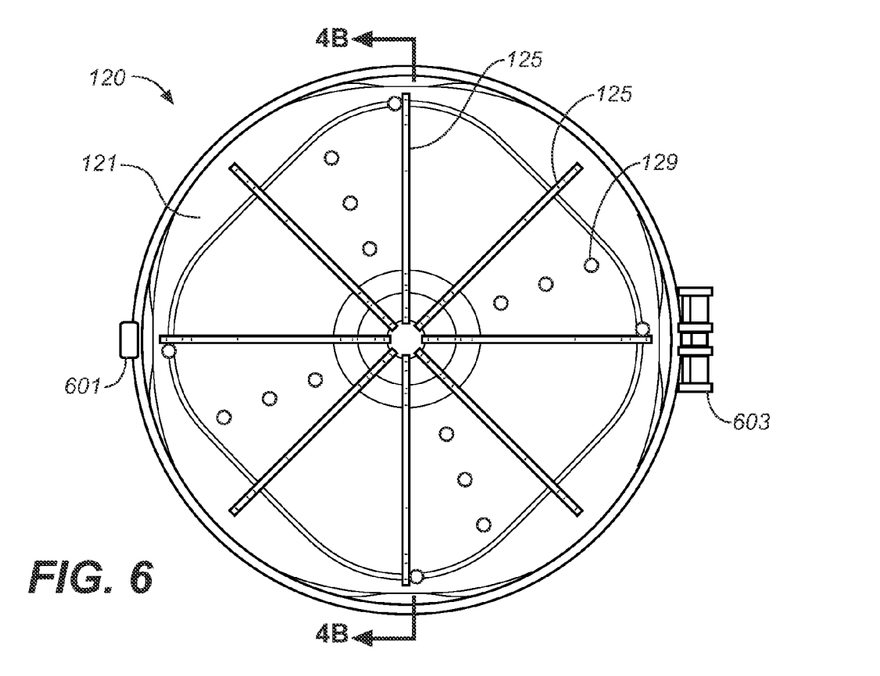
FIG. 6 is a top view 6-6 of the case bottom of FIG. 4B.

The structure of case 100 is shown in greater detail in FIG. 4B, which is an exploded sectional view of FIG. 4A, FIG. 5, which is a bottom view 5-5 of case portion 110, and in FIG. 6, which is a top view 6-6 of case portion 120. Case portion 110 has a domed portion 111 with a rim 113, and several inward and radial ridge or extensions 115 that each has an edge 117, and a first clasp piece 501 and a first hinge piece 503. Case portion 120 has a base 121 with a rim 123, and several inward and radial ridges or extensions 125 that each has an edge 127, and a second clasp piece 601 and a second hinge piece 603. Case bottom 120 also has a plurality of holes 129 through portion 121.

In one embodiment, extensions 115 and 125 protrude into case 100 and form part of surfaces 401 and 403 such that, when the case is closed, edges 117 and 127 approximate the shape of the article to be held, such as that of nipple shield A.

Figure 7A:
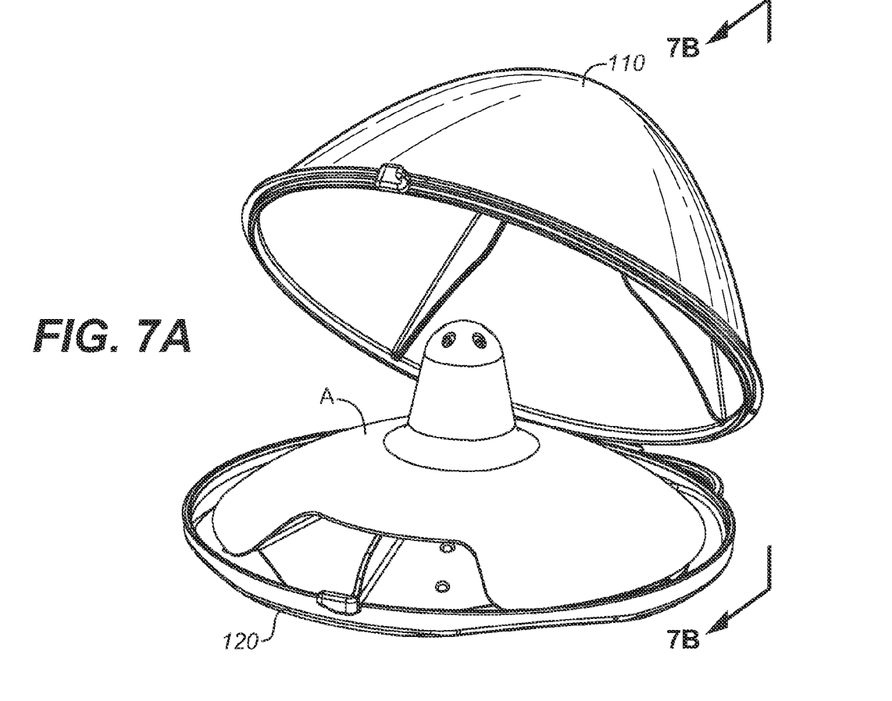
FIG. 7A is a top perspective view of the first embodiment case in an open configuration, with a nipple shield in place.
Figure 7B:
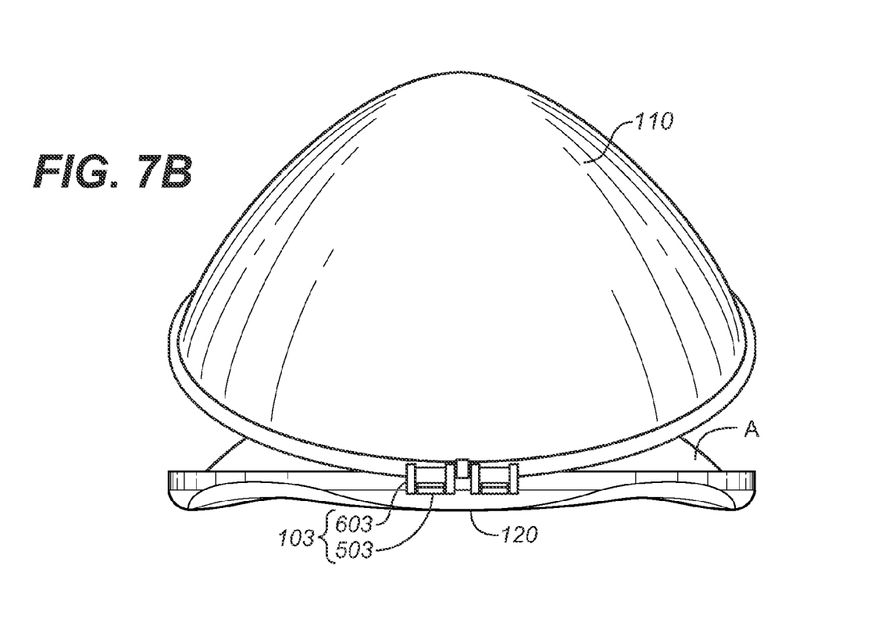
FIG. 7B is a rear elevational view of the first embodiment case in an open configuration.
Figure 7C:
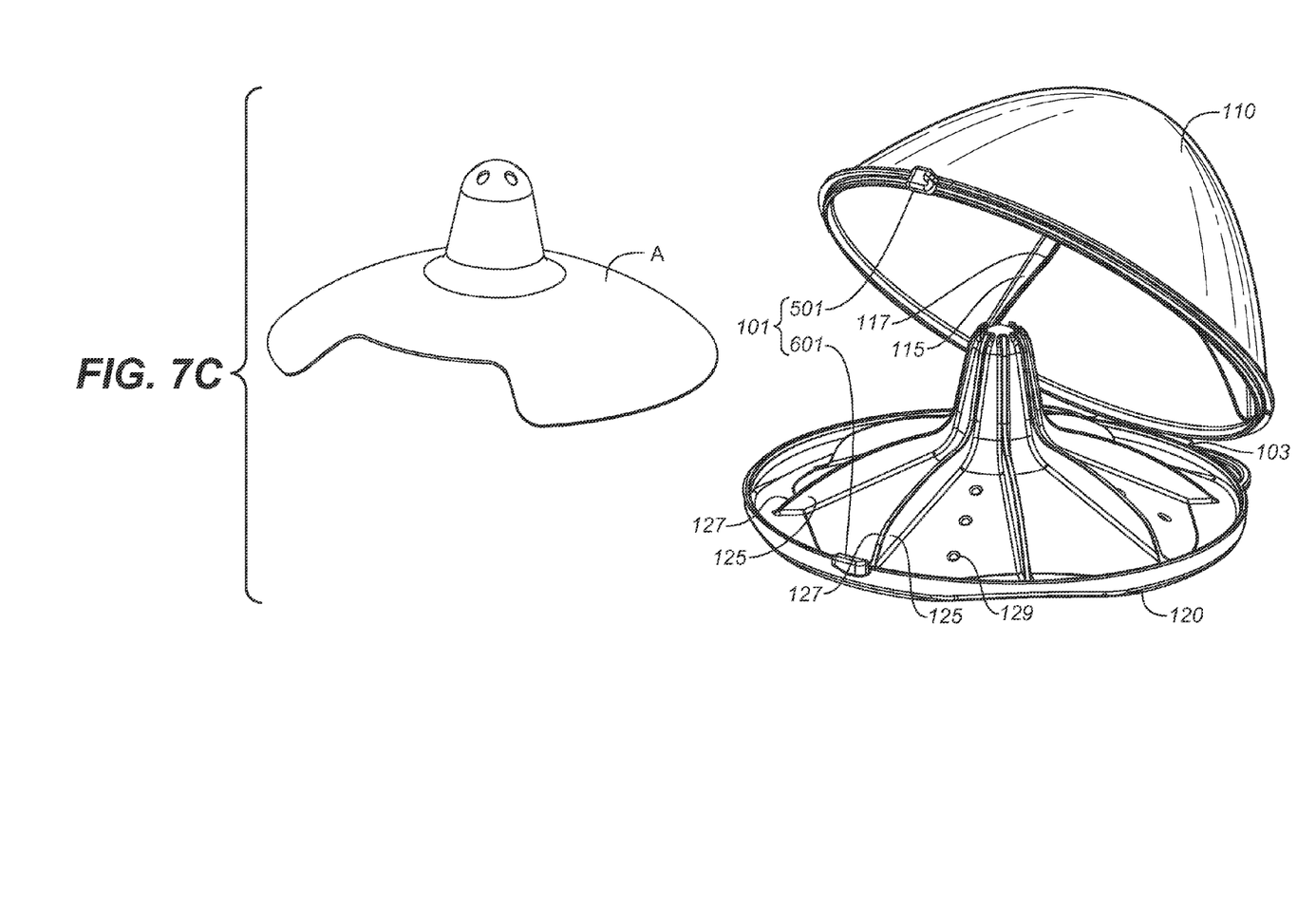
FIG. 7C is a top perspective view of the first embodiment case in an open configuration, with a nipple shield removed.
Figure 8:
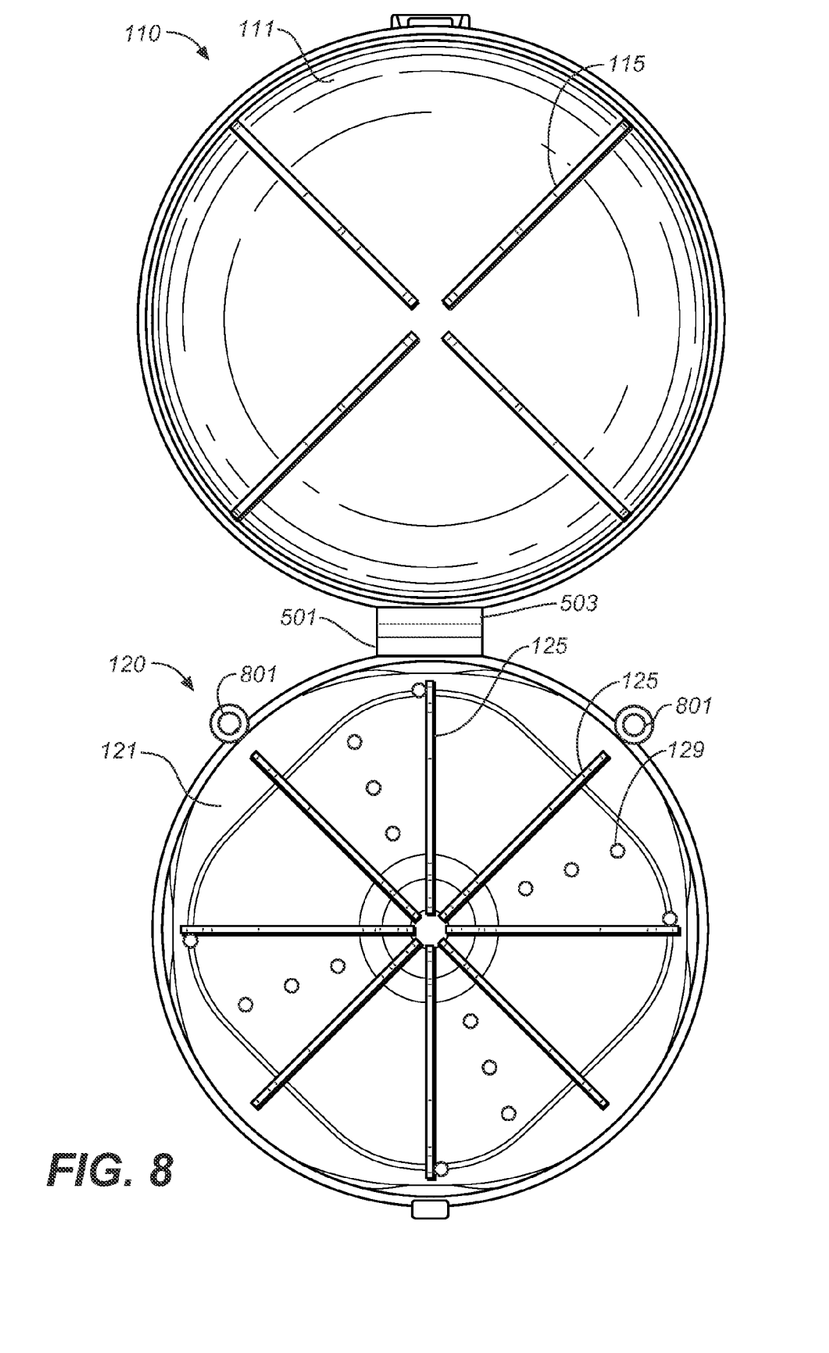
FIG. 8 is a view the first embodiment case in an open configuration.

FIGS. 7A, 7B, and 7C are views of case 100 in an open configuration, where FIG. 7A is a perspective view showing nipple shield A in place, FIG. 7B is a rear elevational view of the case, and FIG. 7C is a perspective view with the nipple shield removed from the case. FIG. 8 is a view the first embodiment case in a fully open configuration, showing the inner surfaces of case portion 110 and 120.

As shown in FIGS. 5, 6, 7A and 7B, clasp 101 works by the cooperation of first clasp piece 501 and second clasp piece 601. Pieces 501 and 601 may interlock when case 100 is closed, and the twisting of the pieces or deforming rims 113 and/or 123 may release clasp 101. The figures also show hinge 103 as being formed from the cooperation of first hinge piece 503 and second hinge piece 603. Pieces 503 and 603 may, for example, include a pin and pin notches to permit the first case portion 110 and second case portion 120 to rotate and allow the case to open or, alternatively, hinge 103 may be an integral part of case top 110 and case bottom 120 that is engineered to bend and work as a hinge.

In certain embodiments, case 100 is formed, for example and without limitation, from polypropylene manufactured by injection molding. Thus, for example, case 100 may be formed by molding a plastic to provide solid portions 111 and 121 and extensions 115 and 125 that are approximately 2 to 4 mm thick. In certain embodiments, there may be from 1 to 12 extensions 115 and 125. In certain other embodiments, there may be from 1 to 20 holes or more, distributed along portion 121. Although rims 113 and 123 are shown as being generally circular, matching rims of other shapes are within the scope of the present invention.

Case 100 thus may be opened, as in FIG. 7C, to allow a user to place nipple shield A within the case, as in FIG. 7A and 7B, and then closed, as in FIG. 4A to contain the nipple shield. The shape of volume V permits the nipple shield to be held in place with the minimum of movement or contact by case 100. Holes 129 allows for the drying of nipple shield A by allowing humid air within volume V to be exchanged with air outside of case 100 and allows the nipple shield to be stored in a clean environment.

As shown in FIG. 8, case 100 may include rings 801 that may be used for attaching a string or chain to the case.

Figure 9:
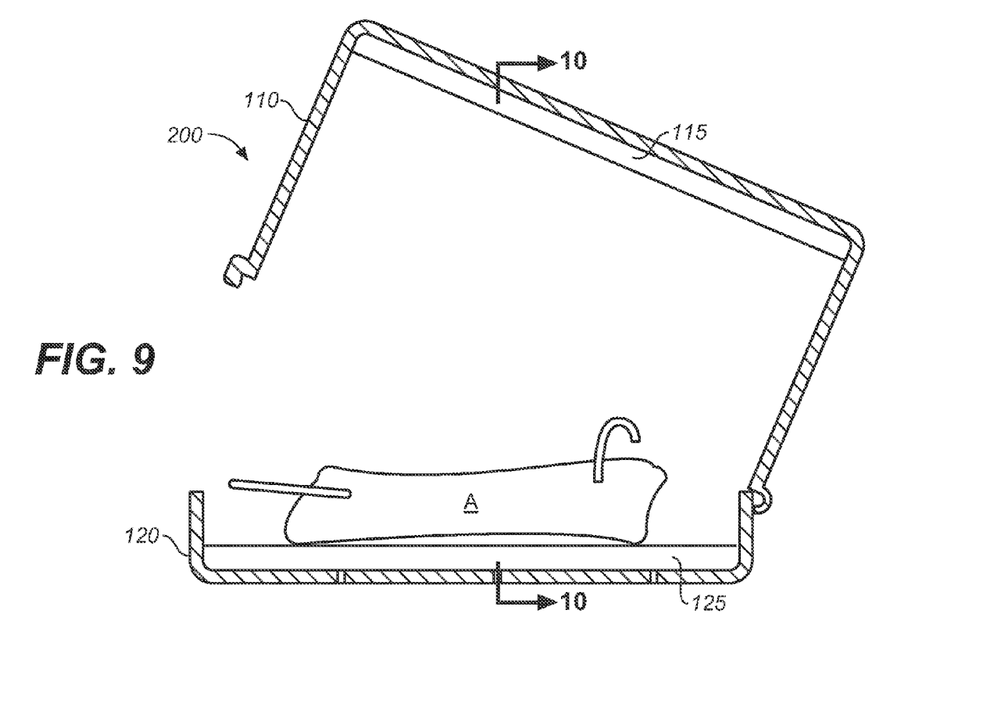
FIGS. 9 and 10 are sectional views of a second embodiment case.
Figure 10:
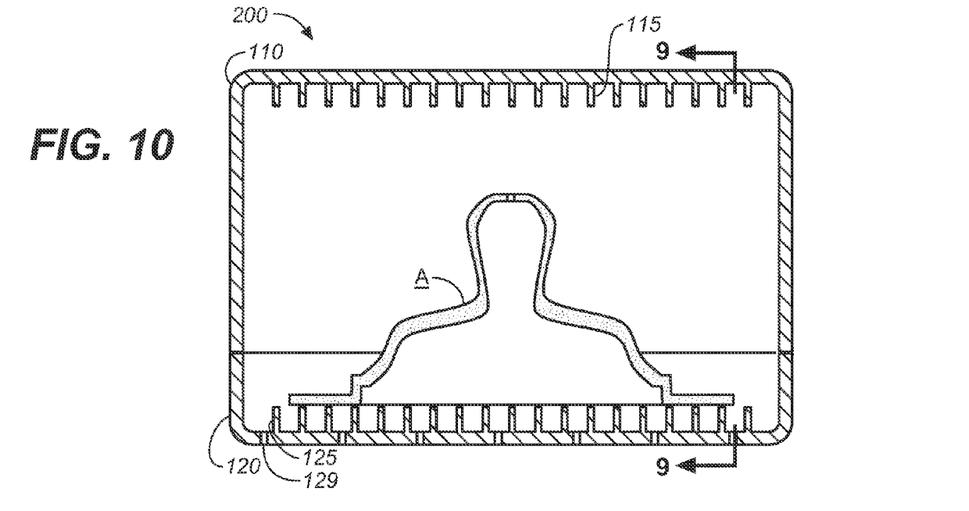

FIGS. 9 and 10 are sectional views of a second embodiment case 200. Case 200 is generally similar to case 100, except as discussed below.

Case 200 illustrates an alternative embodiment, wherein the case is rectangular and ridges 115 and 125 are in a linear arrangement along first case portion 110 and second case portion 120. Case 200 is not specifically shaped for storing any particular article, which may be, for example, a dental retainer in FIG. 9 and a baby bottle nipple in FIG. 10. Case 200 provides for the storage of articles with minimal case contact and having holes 129 for ventilation.

Thus, while there has been described what is believed to be the preferred embodiment of the invention, those skilled in the art will recognize that other and further modifications may be made thereto without departing from the spirit of the invention, and it is intended to claim all such changes and modifications as fall within the scope of the invention. For example, and with out limitation, different clasping and/or hinging mechanisms may be employed, or case top 110 and case bottom 120 may be separate items that snap together to form an enclosed volume, the inner and/or outer geometries may be different and my for example, have oval or square rims 113 and 123 or may be less domed shape to facilitate stacking of the cases.

It should be appreciated that in the above description of exemplary embodiments of the invention, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the Detailed Description are hereby expressly incorporated into this Detailed Description, with each claim standing on its own as a separate embodiment of this invention.

I claim:

1. A case having an interior surface for confining an article, said case comprising:

a first case portion; and a second case portion adapted for engaging said first case portion to define the interior surface, wherein said first case portion includes one or more first ridges having edges that protrude towards said second case portion, and one or more apertures to the exterior of the case, and wherein said second case portion includes one or more second ridges having edges that protrude towards said first case portion, such that an article placed within said case contacts the edges of at least some of the first ridges and the edges of at least some of the second ridges, wherein said edges of said one or more first ridges generally define a convex shape, and wherein said edges of said one or more second ridges generally define a concave shape.

2. The case of claim 1, wherein said first case portion has a first rim, wherein said second case portion has a second rim, and wherein said case has a closed configuration forming said interior surface which said first rim is adjacent to said second rim.

3. The case of claim 2, wherein at least one of said one or more first ridges extends from near said first rim towards the center of said case, and wherein at least one of said one or more second ridges extends from near said second rim towards the center of said case.

4. The case of claim 1, wherein said one or more apertures is from 1 to 20 apertures.

5. The case of claim 1, wherein said one or more first ridges is 3, 4, 5, 6, 7, or 8 ridges.

6. The case of claim 1, wherein said one or more second ridges is 3, 4, 5, 6, 7, or 8 ridges.

7. The case of claim 1, wherein said case is formed from a plastic.

8. A case having an interior surface for confining an article, said case comprising:

a first case portion; and a second case portion adapted for engaging said first case portion to define the interior surface, wherein said first case portion includes one or more first ridges having edges that protrude towards said second case portion, and one or more apertures to the exterior of the case, and wherein said second case portion includes one or more second ridges having edges that protrude towards said first case portion, such that an article placed within said case contacts the edges of at least some of the first ridges and the edges of at least some of the second ridges, wherein said article is a nipple shield or a nipple protector, and wherein said edges of said one or more first ridges and said one or more second ridges approximate the shape of the nipple shield or the nipple protector.

9. The case of claim 1, wherein said one or more first ridges are integral to said first case portion and wherein said one or more second ridges are integral to said second case portion.

10. A case for confining a conical-shaped article, said case comprising:

a first case portion;

a second case portion; and a hinge connecting said first case portion and said second case portion, such that when said first case and said second case are in a closed configuration said case has an interior surface, wherein said first case portion has a first rim and includes one or more first ridges having edges that protrude towards said second case portion, where said edges of said one or more first ridges generally define a convex shape, and one or more apertures to the exterior of the case, and wherein said second case portion has a second rim and includes one or more second ridges having edges that protrude towards said first case portion, where said edges of said one or more second ridges generally define a concave shape, such that an article placed within said case contacts the edges of at least some of the first ridges and the edges of at least some of the second ridges, wherein said article is a nipple shield or a nipple protector, and wherein said edges of said one or more first ridges and said one or more second ridges approximate the shape of the nipple shield or the nipple protector.

11. The case of claim 10, wherein at least one of said one or more first ridges extends from near said first rim towards the center of said case, and wherein at least one of said one or more second ridges extends from near said second rim towards the center of said case.

12. The case of claim 10, wherein said one or more apertures is from 1 to 20 apertures.

13. The case of claim 10, wherein said one or more first ridges is 3, 4, 5, 6, 7, or 8 ridges.

14. The case of claim 10, wherein said one or more second ridges is 3, 4, 5, 6, 7, or 8 ridges.

15. The case of claim 10, wherein said case is formed from a plastic.

16. The case of claim 10, wherein said one or more first ridges are integral to said first case portion and wherein said one or more second ridges are integral to said second case portion.

* * * * *